US008658767B2

(12) United States Patent
Leng et al.

(10) Patent No.: US 8,658,767 B2
(45) Date of Patent: Feb. 25, 2014

(54) LIPIDATED POLYEPITOPE VACCINES

(75) Inventors: Chih-Hsiang Leng, Zhunan Town (TW);
Chi-Ling Tseng, Zhunan Town (TW);
Hsueh-Hung Liu, Zhunan Town (TW);
Shih-Jen Liu, Zhunan Town (TW);
Hsin-Wei Chen, Zhunan Town (TW);
Pele Choi-Sing Chong, Zhunan Town (TW)

(73) Assignee: National Health Research Institutes, Zhunan Town (TW)

( * ) Notice: Subject to any disclaimer, the term of this patent is extended or adjusted under 35 U.S.C. 154(b) by 50 days.

(21) Appl. No.: 13/296,617

(22) Filed: Nov. 15, 2011

(65) Prior Publication Data

US 2012/0121628 A1 May 17, 2012

Related U.S. Application Data

(60) Provisional application No. 61/413,619, filed on Nov. 15, 2010.

(51) Int. Cl.
*A61K 39/15* (2006.01)
*A61K 38/14* (2006.01)

(52) U.S. Cl.
USPC ....................................... 530/350; 424/188.1

(58) Field of Classification Search
None
See application file for complete search history.

(56) References Cited

U.S. PATENT DOCUMENTS

| | | | |
|---|---|---|---|
| 4,745,069 A | 5/1988 | Mayne et al. | |
| 5,942,236 A | 8/1999 | Lobert et al. | |
| 6,013,258 A | 1/2000 | Urban et al. | |
| 6,183,746 B1 | 2/2001 | Urban et al. | |
| 6,361,966 B1 | 3/2002 | Walker et al. | |
| 6,538,118 B1 | 3/2003 | Huebner et al. | |
| 6,582,704 B2 | 6/2003 | Urban et al. | |
| 6,936,263 B2 | 8/2005 | Revets et al. | |
| 7,026,443 B1* | 4/2006 | Sette et al. | 530/300 |
| 7,097,843 B2 | 8/2006 | Urban et al. | |
| 7,235,243 B2 | 6/2007 | Becker et al. | |
| 7,314,629 B2 | 1/2008 | Zagury et al. | |
| 7,569,225 B2 | 8/2009 | Jackson et al. | |
| 7,833,776 B2 | 11/2010 | Leng et al. | |
| 2005/0276813 A1 | 12/2005 | Muhlradt et al. | |
| 2005/0281835 A1 | 12/2005 | Yang | |
| 2009/0074781 A1 | 3/2009 | Chen et al. | |
| 2009/0081253 A1 | 3/2009 | Hanon et al. | |
| 2009/0176273 A1 | 7/2009 | Leng et al. | |
| 2009/0214632 A1* | 8/2009 | Sette et al. | 424/450 |
| 2009/0221499 A1 | 9/2009 | Leng et al. | |
| 2010/0303849 A1 | 12/2010 | Chen et al. | |
| 2010/0322953 A1 | 12/2010 | Leng et al. | |
| 2012/0041179 A1 | 2/2012 | Hsieh et al. | |

FOREIGN PATENT DOCUMENTS

| | | |
|---|---|---|
| CA | 2183416 | 8/1995 |
| CA | 2706101 | 6/2009 |
| CN | 1793335 | 6/2006 |
| EP | 1612218 | 1/2006 |
| EP | 2058002 | 5/2009 |
| GB | 2001/029236 | 4/2011 |
| JP | 2008-113608 | 5/2008 |
| WO | 92/05248 | 4/1992 |
| WO | 92-16636 | 10/1992 |
| WO | 99/10375 | 3/1999 |
| WO | 99/57280 | 11/1999 |
| WO | WO01/00790 | 1/2001 |
| WO | 2004/052395 | 6/2004 |
| WO | 2007/199896 | 10/2007 |
| WO | 2008/049329 | 5/2008 |
| WO | 2008/079372 | 7/2008 |
| WO | 2010/148496 | 12/2010 |

OTHER PUBLICATIONS

Sung, et al. Biochemical characterizations of *Escherichia coli*-expressed protective antigen Ag473 of Neisseria meningitides group B., *Vaccine*. vol. 28(51) Nov. 29, 2010, pp. 8175-8182.
ExPASy—PeptideCutter http://web.expasy.ort/cgi-bin/peptide_cutter/peptidecutter.pl (Accessed Mar. 7, 2012).
Shu, et al. Core Structure of the Outer membrane Lipoprotein from *Escherichia coli* at 1.9A Resolution, (2000) vol. 299, pp. 1101-11112.
Rezwan, et al. "Lipoprotein synthesis in mycobacteria" *Microbiology*. Mar. 2007, vol. 153, pp. 652-658.
Wikman, et al. General strategies for efficient adjuvant incorporation of recombinant subunit immunogents. *Vaccine*. (2005), vol. 23, pp. 2331-2335.
Cote-Sierra, et al. "A New Membrane-Bound Oprl Lipoprotien Expression Vector High Prodcution of Heterologous Fusion Proteins in Gram (-) Bacteria and the Implications for Oral Vaccination" *Gene* (1998) vol. 221, pp. 25-34.
Crill, Wayne D., et al. "Monoclonal Antibodies That Blind to Domain III of Dengue Virus E Glycoprotien Are the Most Efficient Blockers of Virus Adsorption to Vero Cells" *Journal of Virology* (Aug. 2001) pp. 7769-7773.
Chen, W., et al. "Induction of cytotoxic T-lymphocytes and antitumor activity by a liposomal lipopeptide vaccine" *Mol. Pharm.* vol. 5, No. 3 (2008) pp. 464-471.
Jackson, D.C., et al. "A totally synthetic vaccine of generic structure that targets Toll-like receptor 2 on dendritic cells and promotes antibody or cytotoxic T cell responses" *Proc. Natl. Acad. Sci. USA* vol. 101, No. 43 (2004) pp. 1540-15445.
Klein et al., "Molecular Analysis and Nucleotide Sequence of the envCD operon of *Escherichia coli*," Mol. Ben. Genet. 230: 230-240 (1991).
Masconi, et al. "Structural Basis for the Immunogenic Properties of the Meningococcal Vaccine Candidate LP2086" The Journal of Biological Chemistry, vol. 284, No. 13, pp. 8738-8746 (Mar. 27, 2009).
Sivashanmugam, Arun, et al. "Practical protocols for production of very high yields of recombinant proteins using *Escherichia coli*" Protein Science vol. 18, pp. 936-948 (2009).
Babaeipour, Valiollah, et al. "Enhancement of human granulocyte-colony stimulating factor production in recombinant *E. coli* using batch cultivation" Bioprocess Biosyst Eng (2010) pp. 591-598.
Chen, H-W. et al. A novel technology for the production of a heterologous lipoprotein immunogen in high yield has implications for the field of vaccine design. Vaccine. Epub: IS Jan. 2009 (Jan. 15, 2009). vol. 27, pp. 1400-1409.

(Continued)

*Primary Examiner* — Bao Li
(74) *Attorney, Agent, or Firm* — Cesari and McKenna, LLP

(57) ABSTRACT

This invention relates to, inter alia, an isolated lipidated polypeptide including a lipid moiety at the N-terminus and a plurality of epitopes, and methods of making and using the polypeptide.

9 Claims, 3 Drawing Sheets

(56) References Cited

OTHER PUBLICATIONS

Chiung-Yi Huang. "Potential Treatment of Human Papillomavirus Associated Tumors Using Recombinant Inactive-E7 Lipoproteins." Electronic Theses & Dissertations Services; Master Programs of Life Sciences, Aug. 24, 2009. pp. 1-5.

Cullen et al., "Construction and Evaluation of a Plasmid Vector for the Expression of Recombinant Lipoproteins in *Escherichia coli*," Plasmid 49: 18-29 (2003).

De et al., "Purification and Characterization of Streptococcis pneumoniae palmitoylated and pneumococcal surface adhesion A expressed in *Escherichia coli*," Vaccine: 18: 1811-1821 (2000).

Dumon-Seignovert et al., The toxicity of recombinant proteins in *Escherichia coli*: a comparison of overexpression in BL21 (DE3), C41 (DE3), and C43(DE3)., Protein Expression and Purification, vol. 37, Issue 1, Sep. 2004, pp. 203-206.

*E. coli* genotypes (last viewed on Feb. 1, 2011).

Esche, U. v.d. et al. Immunostimulation by bacterial components: I. Activation of macrophages and enhancement of genetic immunization by the lipopeptide P3CSK4. Intl. 1. Immunopharm. Dec. 2000. vol. 22, pp. 1093-1102.

Green et al., The e(P4) Outer membrane Protein of Haemophilus influenzae: biologic activity of Anti-e Serum and Cloning and Sequencing of the Structural Gene., Infection and Immunity, 1991, vol. 59, pp. 3191-3198.

Hsu, C-A. et at. Immunoproteomic identification of the hypothetical protein NMB1468 as a novel lipoprotein ubiquitous in Neisseria meningitidis with vaccine potential. Proteomics. 2008. vol. 8, pp. 2115-2125.

Kamalakkannan et al., "Bacterial Lipid Modification of Proteins for Novel Protein Engineering Applications," Protein, Engineering, Design & Selection 17(10): 721-729 (2004).

Legrain et al., "Production of Lipidated Meningococcal Transferrin Binding Protein 2 in *Escherichia coli*" Protein Expression and Purification 6:570-578 (1995).

Liu, et al. "Structure of the Human Papillomavirus E7 Oncoprotein and its Mechanism for Inactivation ofthe Retinoblastoma Tumor Suppressor", 1. Biol. Chern., Jan. 2006. vol. 281, pp. 578-586.

Steller et al. "Cell-mediated Immunological Responses in Cervical and Vaginal Cancer Patients Immunized with a Lipidated Epitope of Human Papillomavirus Type 16 E7." Clinical Cancer Research, vol. 4, Sep. 1998. pp. 2103-2109.

Chiung-Yi Huang et al. "Recombinant Lipidated HPV E7 Induces a TH-1-Biased Immune Response and Protective Immunity against Cervical Cancer in a Mouse Model," PLOS ONE, 7(7) e40970-e40970 (2012).

\* cited by examiner

FIG. 1

```
Met Lys Lys Leu Leu Ile Ala Ala Met Met Ala Ala Ala Leu Ala
 1               5                  10                  15
Ala Cys Ser Gln Glu Ala Lys Gln Glu Val Lys Glu Ala Val Gln
                20                  25                  30
Ala Val Glu Ser Asp Val Lys Asp Thr Ala Gly Ser Thr Pro Thr
                35                  40                  45
Leu His Glu Tyr Met Leu Asp Leu Gln Pro Glu Thr Thr Asp Leu
                50                  55                  60
Tyr Cys Tyr Glu Cys Thr Glu Leu Gln Thr Thr Ile His Asp Ile
                65                  70                  75
Ile Leu Glu Cys Val Tyr Cys Lys Gln Gln Leu Pro His Ala Ala
                80                  85                  90
Cys His Lys Cys Ile Asp Phe Tyr Ser Arg Ile Arg Glu Leu Arg
                95                  100                 105
His Tyr Ile Arg Thr Leu Glu Asp Leu Leu Met Gly Thr Leu Gly
                110                 115                 120
Ile Val Cys Pro Ile Cys Ser Gln Lys Pro
                125                 130
```

FIG. 2

```
Met Lys Lys Leu Leu Ile Ala Ala Met Met Ala Ala Ala Leu Ala
 1               5                  10                  15
Ala Cys Ser Gln Glu Ala Lys Gln Glu Val Lys Glu Ala Val Gln
                20                  25                  30
Ala Val Glu Ser Asp Val Lys Asp Thr Ala Gly Ser Met Ser Ala
                35                  40                  45
Ala Lys Phe Val Ala Ala Trp Thr Leu Lys Ala Ala Ala Ser Asp
                50                  55                  60
Ser Gly Ile Leu Gly Phe Val Phe Thr Leu Lys Ala Ala Ser Ile
                65                  70                  75
Ile Asn Phe Glu Lys Leu Ala Ala Ala Cys Thr Glu Leu Gln Thr
                80                  85                  90
Thr Ile His Asp Ile Ile Leu Glu Cys Val Tyr Cys Lys Gln Gln
                95                  100                 105
Leu Pro His Ala Ala Cys His Lys Cys Ile Asp Phe Tyr Ser Arg
                110                 115                 120
Ile Arg Glu Leu Arg His Tyr Thr Pro Thr Leu His Glu Tyr Met
                125                 130                 135
Leu Asp Leu Gln Pro Glu Thr Thr Asp Leu Tyr Cys Tyr Glu Ile
                140                 145                 150
Arg Thr Leu Glu Asp Leu Leu Met Gly Thr Leu Gly Ile Val Cys
                155                 160                 165
Pro Ile Cys Ser Gln Glu Asp Leu Leu Met Gly Thr Leu Gly Ile
                170                 185                 190
Val Cys Pro Ile Cys Ser Gln Lys Pro Ala Asp Asp Leu Arg Ala
                195                 200                 205
Phe Gln Gln Leu Phe Leu Asn Thr Leu Ser Phe Val Cys Pro Trp
                210                 215                 220
```

LIPIDATED POLYEPITOPE VACCINES

CROSS REFERENCE TO RELATED APPLICATIONS

This application claims priority to U.S. Provisional Application No. 61/413,619, filed Nov. 15, 2010, the content of which is incorporated herein by reference in its entirety.

BACKGROUND

The use of epitopes identified from pathogens as target antigens is an important strategy for developing therapeutic vaccines. Immunization with polyepitopes would provide advantages over single epitope-based vaccines. Thus far, development of polyepitope vaccines has mainly been focused on DNA vaccines. However, there are various safety concerns regarding DNA vaccines. There is a need to develop polyepitope vaccines that can overcome the obstacle of DNA-based vaccines.

SUMMARY

This invention is based on the discovery that lipidated polypeptides containing multiple epitopes, when administered to a subject, can induce an immune response in the subject.

In one aspect, described herein is an isolated lipidated polypeptide including a lipid moiety at the N-terminus and a plurality of epitopes. Each epitope of the plurality can be different. In some embodiments, all epitopes of the plurality are cytotoxic T lymphocyte (CTL) epitopes.

All epitopes of the plurality can be from a single pathogen, e.g., human papillomavirus (HPV). In some cases, the plurality of epitopes include one or more epitopes on E6 or E7. In some cases, the plurality of epitopes include different HLA-A2-restricted epitopes of HPV type-16 and type-18, e.g., one or more or all of the peptides listed in Table 1. In some embodiments, the epitopes of the plurality are contiguous or noncontiguous. In some embodiments, the polypeptide is rlipo-A21618-D47 or rlipo-A21618-SDSK.

In another aspect, a composition comprising the lipidated polypeptide described herein is contemplated.

In yet another aspect, also described herein is a method of producing the lipidated polypeptide. The method includes providing an E. coli host cell that has an expression vector including a nucleic acid encoding a polypeptide, the polypeptide having a bacterial lipoprotein signal peptide and the plurality of epitopes; and culturing the E. coli host cell to allow expression of the polypeptide in lipidated form, thereby producing the lipidated polypeptide. In some embodiments, the nucleic acid is codon-optimized for expression in E. coli. In some cases, the lipoprotein signal peptide comprises the D1 domain of Ag473.

In yet another aspect, described herein is a method of eliciting an immune response in a subject, the method includes administering to the subject a composition containing the lipidated polypeptide. The immune response can be a CTL-mediated immune response. The invention also contemplates a method for treating a human papillomavirus (HPV)-associated disease. The method includes administering to a subject in need thereof an effective amount of a composition containing the lipidated polypeptide described herein.

Also included in this invention is a use of the above-described polypeptide or composition for eliciting an immune response or for treating an HPV-associated disease in a subject.

An "antigen" refers to a molecule containing one or more epitopes that will stimulate a host's immune system to make a humoral and/or cellular antigen-specific response. The term "antigen" is used interchangeably with "immunogen." As a result of coming in contact with appropriate cells, an "antigen" induces a state of sensitivity or immune responsiveness and reacts in a demonstrable way with antibodies or immune cells of the sensitized subject in vivo or in vitro. An "antigen" can be specifically recognized and bound by antibodies in an organism. An antigen in association with a major histocompatibility complex (MHC) can also be recognized and bound by receptors on the surface of T lymphocytes (T-cells), leading to the activation of the T-cells.

The term "epitope" as used herein refers to the site on an antigen recognized by antibodies or immune cells, e.g., B-cells and T-cells. The term "epitope" is used herein interchangeably with "antigenic determinant" or "antigenic determinant site." A cytotoxic T-cell (CTL) epitope refers to an epitope capable of activating a CTL (also known as Tc or killer T cell), which subsequently stimulates CTL responses, i.e., inducing death of abnormal cells (e.g., virus-infected or tumor cells). A CTL epitope, typically including 8-11 amino acid residues, forms a complex with a particular MHC class 1 molecule (including a heavy chain and a β2 microglobulin) presented on the surface of an antigen-presenting cell. This complex, upon binding to a T cell receptor of a $CD_8$ T cell (a CTL), activates the T cell, thus triggering CTL responses.

The term "immune response" or "immunogenic response" refers to any reaction of the immune system in response to an antigen in a subject. Examples of an immune response in a vertebrate include, but are not limited to, antibody production, induction of cell-mediated immunity, complement activation, and development of immune tolerance. The immune response to a subsequent stimulus by the same antigen, also named the secondary immune response, can be more rapid than in the case of the primary immune response.

A "subject" refers to a human and a non-human animal. Examples of a non-human animal include all vertebrates, e.g., mammals, such as non-human primates (particularly higher primates), dog, rodent (e.g., mouse or rat), guinea pig, cat, and non-mammals, such as birds, amphibians, etc. In a preferred embodiment, the subject is a human. In another embodiment, the subject is an experimental animal or animal suitable as a disease model.

The term "treating" as used herein refers to the application or administration of a composition including one or more active agents to a subject, who has a disease, a symptom of the disease, or a predisposition toward the disease, with the purpose to cure, heal, alleviate, relieve, alter, remedy, ameliorate, improve, or affect the disease, the symptoms of the disease, or the predisposition toward the disease. "An effective amount" as used herein refers to the amount of each active agent required to confer therapeutic effect on the subject, either alone or in combination with one or more other active agents. Effective amounts vary, as recognized by those skilled in the art, depending on route of administration, excipient usage, and co-usage with other active agents.

The term "isolated" as used herein with reference to a polypeptide refers to a polypeptide substantially free from naturally associated molecules; namely, it is at least 60% (i.e., about 65, 70, 75, 80, 85, 90, 95, or 99 percent) pure by dry weight. Purity can be measured by any appropriate method, e.g., column chromatography, polyacrylamide gel electrophoresis, and HPLC.

The term "lipoprotein signal peptide" or "lipid signal peptide" refers to a peptide found on naturally-occurring lipoprotein or a variant thereof that facilitates lipidation of a polypeptide carrying the signal peptide at its N-terminus.

The details of one or more embodiments of the invention are set forth in the accompanying drawing and the description below. Other features, objects, and advantages of the invention will be apparent from the description and drawing, and from the claims.

BRIEF DESCRIPTION OF DRAWINGS

FIG. 1 is a table showing the amino acid sequences of rA21618-D47 (SEQ ID NO:1) and rlipo-A21618-D47 (SEQ ID NO:2). The underlined portion is the sequence of rA21618-D47. rlipo-A21618-D47 includes the amino acid sequence of rA21618-D47 plus a lipid signal peptide at the N-terminus.

FIG. 2 is a table showing the amino acid sequences of rA21618-SDSK (SEQ ID NO:3) and rlipo-A21618-SDSK (SEQ ID NO:4). The underlined portion is the sequence of rA21618-SDSK. rlipo-A21618-SDSK includes the amino acid sequence of rA21618-SDSK plus a lipid signal peptide at the N-terminus.

DETAILED DESCRIPTION

Figure 3:
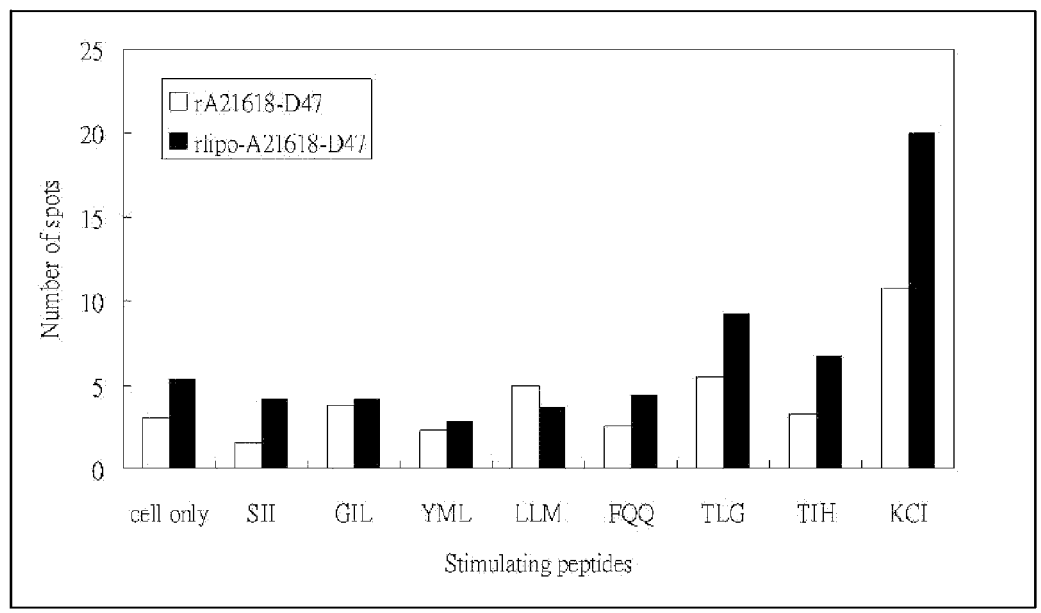
FIG. 3 is a bar graph showing induction of epitope-specific CTL response in HLA-A2-transgenic mice by rA21618-D47 and rlipo-A21618-D47.

Described herein is a lipidated polypeptide including a lipid moiety at the N-terminus and a plurality of epitopes, and methods of making and using them.

The lipidated polypeptide of the present invention includes a plurality of epitopes, e.g., at least two. The epitopes in the lipidated polypeptide can be contiguous or separated by linker amino acid sequences. Each linker in a lipidated polypeptide can be the same or different. A linker can include up to 8 amino acids (e.g., 1, 3, 6 or 8). Those of ordinary skill in the art would appreciate that there are many possible configurations of epitopes and linkers.

The epitopes of the lipidated polypeptide can be any epitopes known in the art. Epitopes identified using methods known in the art can also be used to generate the lipidated polypeptide. The plurality of epitopes in a particular lipidated polypeptide can be all from the same pathogen. In some embodiments, the plurality of epitopes are CTL epitopes. Examplary epitopes useful for the present invention include those described in U.S. Application Pub. No. 2009/0117123, U.S. patent application Ser. No. 12/787,539, Duraiswamy et al. (2003, J. Virology. 77:7401-10) and Lutzky et al. (2010 J. Virology. 84:407-417).

The lipidated polypeptide of the invention can be obtained as a synthetic polypeptide or a recombinant polypeptide. A lipoprotein signal peptide or lipid signal peptide can be linked to a target polypeptide, e.g., one that contains a plurality of epitopes, by conventional recombinant technology to form a fusion protein, which is in lipidated form when expressed in *E. coli*. Examples of lipoprotein signal peptides include those described in U.S. Pat. Pub. No. 2009/0221499.

For example, to produce a lipidated polypeptide, a DNA fragment encoding the lipoprotein signal peptide and a DNA fragment encoding the target polypeptide are inserted into an expression vector, preferably carrying a strong promoter (e.g., T7, T5, T3, or SP6), to construct an expression plasmid. The strong promoter can be inducible, e.g., by isopropyl β-D-thiogalactoside (IPTG). The expression plasmid is then introduced into an *E. coli* host strain and positive transformants are cultured under suitable conditions for protein expression. It is preferred that the *E. coli* host strain be resistant to the toxic effects induced by over-expression of exogenous proteins. Such *E. coli* strains can be identified or generated by the methods described in U.S. Pat. No. 6,361,966. Examples of these *E. coli* strains include, but are not limited to, C43(DE3) (ECCC B96070445), C41(DE3) (ECCC B96070444), C0214(DE3), DK8(DE3)S (NCIMB 40885), and C2014(DE3) (NCIMB 40884).

Preferably, the fusion protein thus expressed is isolated from the *E. coli* host cells and its lipidation status is confirmed via methods known in the art, e.g., immunoblotting with an anti-lipoprotein antibody or mass spectrometry.

Useful lipoprotein signal peptides include the signal peptide of *E. coli* acriflavine-resistance protein E precursor and the signal peptide of *Neisseria meningitides* Ag473 protein. Lipoprotein signal peptides can be identified by, for example, identifying the signal peptide on natural lipoproteins (e.g., those listed in the DOLOP database at mrc-lmb.cam.ac.uk/genomes/dolop/). Variants of naturally-occurring lipoprotein signal peptides can also be used.

Also described herein is a composition including the lipidated polypeptide of the present invention. The composition can be prepared according to any methods known in the art. For example, the composition can contain an effective amount of the lipidated polypeptide of the invention, and a pharmaceutically acceptable carrier such as a phosphate buffered saline, a bicarbonate solution, or an adjuvant. The carrier must be "acceptable" in the sense that it is compatible with the active ingredient of the composition, and preferably, capable of stabilizing the active ingredient and is not deleterious to the subject to be treated. The carrier is selected on the basis of the mode and route of administration, and standard pharmaceutical practice. Suitable pharmaceutical carriers and diluents, as well as pharmaceutical necessities for their use, are described in Remington's Pharmaceutical Sciences. An adjuvant, e.g., a cholera toxin, *Escherichia coli* heat-labile enterotoxin (LT), liposome, immune-stimulating complex (ISCOM), or immunostimulatory sequences oligodeoxynucleotides (ISS-ODN), can also be included in a composition of the invention, if necessary. The composition can also include a polymer that facilitates in vivo delivery. See Audran R. et al. Vaccine 21:1250-5, 2003; and Denis-Mize et al. Cell Immunol., 225:12-20, 2003.

The above-described lipidated polypeptide can be used in an immunogenic composition, e.g., a vaccine, for generating antibodies and immune response against a pathogen in a subject susceptible to the pathogen. Exemplary pathogens include, but are not limited to human papillomavirus (HPV), hepatitis C virus (HCV), Epstein-Barr virus (EBV), herpes simplex virus 1 (HSV-1), herpes simplex virus 2 (HSV-2), cytomegalovirus (CMV), respiratory syncytial virus (RSV), parainfluenza virus type 3 (PIV3), influenza viruses, dengue virus, west Nile virus, Norovirus, and SARS coronavirus, Methods for preparing vaccines are well known in the art, as exemplified by U.S. Pat. Nos. 4,601,903; 4,599,231; 4,599, 230; and 4,596,792. Vaccines can be prepared as injectables, as liquid solutions or as emulsions. The lipidated polypeptide of this invention may be mixed with physiologically acceptable excipients. Excipients can include, water, saline, dextrose, glycerol, ethanol, and combinations thereof. The vaccine can further contain minor amounts of auxiliary substances such as wetting or emulsifying agents, pH buffering agents, or an adjuvant to enhance the effectiveness of the vaccines. Methods of achieving adjuvant effect for the vaccine include use of agents, such as aluminum hydroxide or phosphate (alum), commonly used as 0.05 to 0.1 percent solutions in phosphate buffered saline. Vaccines can be administered parenterally, subcutaneously or intramuscularly. Alternatively, other modes of administration including suppositories and oral formulations may be desirable. For suppositories, binders and carriers can include, for example, polyalkalene glycols or triglycerides. Oral formulations can include normally employed incipients such as pharmaceutical grade saccharine, cellulose, magnesium carbonate and the like. These compositions can take the form of solutions, suspensions, tablets, pills, capsules, sustained release formulations or powders and contain 10-95% of the immunopeptide described herein.

The vaccine is administered in a manner compatible with the dosage formulation, and in an amount that is therapeutically effective, protective and immunogenic. The quantity to be administered depends on the subject to be treated, including, for example, the capacity of the individual's immune system to synthesize antibodies, and if needed, to produce a cell-mediated immune response. Precise amounts of active ingredient required to be administered depend on the judgment of the practitioner. However, suitable dosage ranges are readily determinable by one skilled in the art and can be of the order of micrograms of the polypeptide of this invention. Suitable regimes for initial administration and booster doses are also variable, but may include an initial administration followed by subsequent administrations. The dosage of the vaccine may also depend on the route of administration and varies according to the size of the host.

For example, a subject susceptible to HPV infection can be identified and administered the composition described above. The dose of the composition depends, for example, on the particular lipidated polypeptide, whether an adjuvant is co-administered with the lipidated polypeptide, the type of adjuvant co-administered, and the mode and frequency of administration, as can be determined by one skilled in the art. Administration is repeated, if necessary, as can be determined by one skilled in the art. For example, a priming dose can be followed by three booster doses at weekly intervals. A booster shot can be given at 4 to 8 weeks after the first immunization, and a second booster can be given at 8 to 12 weeks, using the same formulation. Serum sample or T-cells can be taken from the subject to determine the immune response elicited by the vaccine against the HPV E6 or E7 protein. Methods of assaying cytotoxic T cells against a protein or infection are well known in the art. Additional boosters can be given as needed. By varying the amount of the lipidated polypeptide, the dose of the composition, and frequency of administration, the immunization protocol can be optimized for eliciting a maximal immune response. Efficacy of the composition may also be tested. In an efficacy testing, a non-human subject can be administered via an oral or parenteral route with a composition of the invention. After the initial administration or after optional booster administration, both the test subject and the control subject (receiving mock administration) are challenged with an HPV. End points other than lethality can be used. Efficacy is determined if subjects receiving the composition are free from HPV infection or develop symptoms associated with HPV infection at a rate lower than control subjects. The difference should be statistically significant.

The specific example below is to be construed as merely illustrative, and not limitative of the remainder of the disclosure in any way whatsoever. Without further elaboration, it is believed that one skilled in the art can, based on the description herein, utilize the present invention to its fullest extent. All publications cited herein are incorporated by reference in their entirety.

Example

Whether lipidated polypeptides containing polyepitopes could induce epitope-specific immune responses was investigated. Several HLA-A2-restricted CTL epitopes of HPV type-16 and type-18 were used to construct polyepitope vaccines. A lipid signal peptide was added to the N-terminus of the polypeptides to form the lipidated polyepitope vaccines, rlipo-A21618-SDSk and rlipo-A21618-D47. These recombinant polyepitopes vaccines contain epitopes of HPV type-16 and type-18, which are major pathogens that cause cervical cancer. HLA-A2-transgenic mice were immunized subcutaneously with these lipidated polyepitope vaccines. Data show that both rlipo-A21618-SDSk and rlipo-A21618-D47 can induce epitope-specific CTL response in HLA-A2-transgenic mice.

The selection of epitopes was based on the previous identified HPV16 and HPV18 CTL epitopes for HLA-A2. See Table 1. The extended N- and C-terminal six amino acids flanking each epitope were also selected. All epitopes and their flanking region were concatenated in different order to form A21618-D47 and A21618-SDSK. See, FIGS. 1 and 2. In the case of A21618-SDSK, a helper T cell epitope (PADRE), one mouse MHC class I epitope, and an HLA-A2 epitope from influenza A matrix protein were also included. In order to improve the expression of polyepitope proteins in E. coli, some amino acids were changed according to the hydropathy analysis using TMHMM, PSORTb, and SOSUI software. A lipobox-containing signal peptide was added to the N-terminus of the polyepitopes proteins to form lipidated polyepitopes. The DNA sequences of both polyepitopes were synthesized in vitro by PRISMA Biotech Corporation.

TABLE 1

Names and sequences of epitopes

| Name | Source | Sequence |
|------|--------|----------|
| SII | Mouse control epitope | S I I N F E K L (SEQ ID NO: 5) |
| GIL | HLA-A2 control epitope | G I L G F V F T L (SEQ ID NO: 6) |
| YML | HPV16 | Y M L D L Q P E T T (SEQ ID NO: 7) |
| LLM | HPV16 | L L M G T L G I V (SEQ ID NO: 8) |
| FQQ | HPV18 | F Q Q L F L N T L (SQ ID NO: 9) |
| TLG | HPV16 | T L G I V C P I (SEQ ID NO: 10) |
| TIH | HPV16 | T I H D I I L E C V (SEQ ID NO: 11) |
| KCI | HPV18 | K C I D F Y S R I (SEQ ID NO: 12) |

The A21618-D47 nucleotide sequence was amplified using the forward primer, 5'-GGAATTCCATATGACCCCGAC-CCTGCA-3' (SEQ ID NO:13), which contains an NdeI restriction site, and the reverse primer, 5'-CCGCTCGAGCG-GTTTCTGGCTGCAAATC-3' (SEQ ID NO:14), which is complementary to the coding sequence and contains an XhoI restriction site. The 5' primer for amplification of the A21618-SDSK nucleotide sequence was 5'-CGGGATCCAT- GAGCGCGGCGAAATTTG-3' (SEQ ID NO:15) and the 3' primer was 5'-CCGCTCGAGCCACGGACACACAAAG-3' (SEQ ID NO:16). The PCR products were cloned into the expression vector pET-22b (+). To express proteins, the plasmid was transformed into the E. coli BL21 (DE3) strains and the bacteria were incubated at 37° C. overnight. The expression of rA21618-D47 and rA21618-SDSK were induced with 1 mM IPTG for 3-4 h at 37° C. and cells were harvested by centrifugation.

After induction, cell cultures were centrifuged (8000×g for 20 min) and the pellets were re-suspended in homogenization buffer (20 mM Tris-Cl, 500 mM NaCl, 10% glycerol, 50 mM sucrose, pH 8.0). The cells were disrupted with a French Press (Constant Systems, Daventry, UK) at 27 Kpsi and the cell pellets were clarified by centrifugation (80,000×g for 40 min). The induced rA21618-D47 was washed with 2M urea/PBS pH 7.2 and extracted from the cell pellet using 4M urea/PBS, pH 7.2. The expressed rA21618-SDSK was washed with homogenization buffer containing 3 M guanidine hydrochloride and extracted from the cell pellet using homogenization buffer containing 6 M guanidine hydrochloride. The extracted proteins were both purified using an IMAC column (Ni-NTA resin). On-column folding procedure was used to prepare the soluble form of rA21618-D47 and rA21618-SDSK free of chaotropic agents. LPS was removed by on-column wash with 0.1% of Triton X-114. The amount of residual LPS in rA21618-D47 and rA21618-SDSK were below 100 EU/mg. The endotoxin-free proteins were dialyzed against PBS for animal experiments.

To express rlipo-A21618-D47 and rlipo-A21618-SDSK, the PCR products of A21618-D47 and rA21618-SDSK were cloned into an expression vector, pET-22b (+) containing the D1 sequence from rAg473, using BamHI and XhoI sites. The expression plasmids were transformed into the E. coli C43 (DE3) strain. The transformed cells were grown aerobically overnight in LB medium at 37° C. The overnight culture was transferred to the M9 medium at a ratio of 1:25 and grown aerobically in the shaking incubator (200 rpm) at 37° C. The expression of rlipo-A21618-D47 and rlipo-A21618-SDSK was induced with 1 mM IPTG at 20° C. for 20 h and 25° C. for 16 h respectively. The cells were harvested by centrifugation. The collected cells were re-suspended in homogenization buffer and disrupted by French Press (Constant Systems, Daventry, UK) at 27 kpsi. The cell pellets containing the induced rlipo-A21618-D47 and rlipo-A21618-SDSK were clarified by centrifugation (80,000 g for 30 min) and extracted from the cell pellet using 20 mM Tris (pH 8.9)/1% Triton X-100 and 50 mM Tris (pH 8.9)/1% Triton X-100 respectively. The extracted proteins were purified using an IMAC column (Ni-NTA resin). Triton X-100 was washed out during the purification. LPS was removed by on-column wash with 0.1% of Triton X-114. The amount of residual LPS in rlipo-A21618-D47 and rlipo-A21618-SDSK were below 100 EU/mg. The endotoxin-free lipoproteins were dialyzed against PBS for animal experiments.

The amino acid sequences of rA21618-D47, rlipo-A21618-D47, rA21618-SDSK, or rlipo-A21618-SDSK are shown in FIGS. 1 and 2.

Four groups of HLA-A2-transgenic mice (3 per group) were respectively administered subcutaneously with rA21618-D47, rlipo-A21618-D47, rA21618-SDSK, or rlipo-A21618-SDSK. Each mouse received two doses of 30 µg of each polypeptide in PBS buffer on Days 0 and 14. Mice were sacrificed on Day 21 and their spleens were collected. The spleens were meshed to generate a single cell suspension in RPMI 1640 medium. The cell suspension was centrifuged at 1500 rpm for 5 minutes to pellet the cells. The pellet was re-suspended in 10 ml of RPMI 1640 medium and red cells were lysed using erythrocyte lysing buffer (0.15 M $NH_4Cl$, 10 mM $KHCO_3$, 0.1 mM $Na_2EDTA$) for 1 min at room temperature. Cells were then washed with RPMI 1640 medium and re-suspended in complete RPMI 1640 medium (RPMI 1640 medium supplemented with 10% FBS and 1% mixture of penicillin, streptomycin, and L-glutamate). Cell concentration in suspension was calculated and adjusted to a concentration of $5 \times 10^6$ cells per ml.

Figure 4:
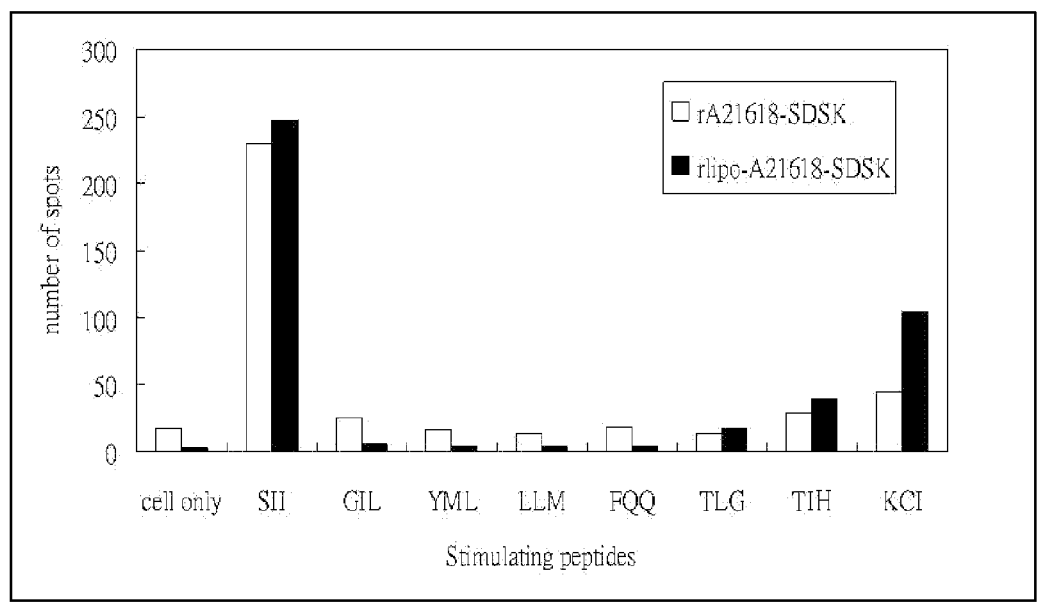
FIG. 4 is a bar graphs showing induction of epitope-specific CTL response in HLA-A2-transgenic mice by rA21618-SDSK and rlipo-A21618-SDSK.

Splenocyte were plated at $5 \times 10^5$ cells per well and cultured with 10 µg/ml of peptides for 48 h, followed by a gamma interferon (IFN-γ) enzyme-linked immunospot (ELISPOT) assay (eBioscience, San Diego, Calif.). The wells of 96-well plates with nitrocellulose membrane inserts were coated with 50 µl of anti-IFN-γ antibody solution (clone AN18, 10 µg/ml in 1×PBS; eBioscience) and incubated for 18 h at 4° C. The plates were then washed with PBS twice and blocked with 100 µl of complete RPMI medium per well for 1 to 3 h to prevent nonspecific binding in later steps. Next, $5 \times 10^5$ splenocytes with 10 µg/ml of the peptides shown in Table 1 above were added to the plate at a final volume of 200 µl. The ELISPOT assay was performed in triplicate for each experimental condition. Specifically, the plates were incubated in a humidified atmosphere of 5% $CO_2$ in air at 37° C. for 48 h. After this incubation, the cells were removed from the plate by washing three times with 0.05% (wt/vol) Tween 20 in PBS. A 50-µl aliquot of biotinylated anti-IFN-γ antibody (clone R46A2, 2 µg/ml in PBS; eBioscience) was then added to each well. The plates were again incubated at room temperature for 2 h. The washing steps were repeated. After 45 minutes of incubation with an avidin-HRP complex reagent (eBioscience) at room temperature, the plates were washed again three times with 0.05% (wt/vol) Tween 20 in PBS and then twice with PBS alone. A 100-µl aliquot of 3-amine-9-ethyl carbazole (AEC; Sigma-Aldrich, St. Louis, Mo.) staining solution was added to each well to develop the spots. The reaction was stopped after 4 to 6 min by placing the plate under tap water. The spots were then counted using an ELISPOT reader (Cellular Technology Ltd., Shaker Heights, Ohio). Both rlipo-A21618-SDSk and rlipo-A21618-D47 induced epitope-specific CTL response in HLA-A2-transgenic mice. See FIGS. 3 and 4.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

What is claimed is:

1. An isolated lipidated polypeptide comprising a lipid moiety at the N-terminus and a plurality of epitopes that includes YMLDLQPETT (SEQ ID NO:7), LLMGTLGIV (SEQ ID NO:8), FQQLFLNTL (SEQ ID NO:9), TLG1VCPI (SEQ ID NO: 10), TIHDIILECV (SEQ ID NO:11), and KCIDFYSRI (SEQ ID NO:12), wherein the polypeptide contains Ihe amino acid sequence of SEP ID NO:1 or 3.

2. The polypeptide of claim 1, wherein the polypeptide includes the amino acid sequence of SEQ ID NO:1 or 3.

3. The polypeptide of claim 1, wherein the polypeptide includes the amino acid sequence of SEQ ID NO:1.

4. The polypeptide of claim 2, wherein the polypeptide includes the amino acid sequence of SEQ ID NO:4.

5. The polypeptide of claim 3, wherein the polypeptide includes the amino acid sequence of SEQ ID NO:2.

6. A composition comprising the lipidated polypeptide of claim 1.

7. A method of eliciting an immune response in a subject, the method comprising administering the composition of claim 6 to a subject in need thereof.

8. The method ol claim 7, wherein the immune response is a CTL-mediated immune response.

9. A method of treating an HPV-associated disease, the method comprising administering the composition containing the lipidated polypeptide of claim 6 to a subject in need thereof.

* * * * *

SEQUENCE LISTING

<160> NUMBER OF SEQ ID NOS: 16

<210> SEQ ID NO 1
<211> LENGTH: 88
<212> TYPE: PRT
<213> ORGANISM: Artificial sequence
<220> FEATURE:
<223> OTHER INFORMATION: Synthetic polypeptide

<400> SEQUENCE: 1

Thr Pro Thr Leu His Glu Tyr Met Leu Asp Leu Gln Pro Glu Thr Thr
1               5                   10                  15

Asp Leu Tyr Cys Tyr Glu Cys Thr Glu Leu Gln Thr Thr Ile His Asp
            20                  25                  30

Ile Ile Leu Glu Cys Val Tyr Cys Lys Gln Gln Leu Pro His Ala Ala
        35                  40                  45

Cys His Lys Cys Ile Asp Phe Tyr Ser Arg Ile Arg Glu Leu Arg His
    50                  55                  60

Tyr Ile Arg Thr Leu Glu Asp Leu Leu Met Gly Thr Leu Gly Ile Val
65                  70                  75                  80

Cys Pro Ile Cys Ser Gln Lys Pro
                85

<210> SEQ ID NO 2
<211> LENGTH: 130
<212> TYPE: PRT
<213> ORGANISM: Artificial sequence
<220> FEATURE:
<223> OTHER INFORMATION: Synthetic polypeptide

<400> SEQUENCE: 2

Met Lys Lys Leu Leu Ile Ala Ala Met Met Ala Ala Ala Leu Ala Ala
1               5                   10                  15

Cys Ser Gln Glu Ala Lys Gln Glu Val Lys Glu Ala Val Gln Ala Val
            20                  25                  30

Glu Ser Asp Val Lys Asp Thr Ala Gly Ser Thr Pro Thr Leu His Glu
        35                  40                  45

Tyr Met Leu Asp Leu Gln Pro Glu Thr Thr Asp Leu Tyr Cys Tyr Glu
    50                  55                  60

Cys Thr Glu Leu Gln Thr Thr Ile His Asp Ile Ile Leu Glu Cys Val
65                  70                  75                  80

Tyr Cys Lys Gln Gln Leu Pro His Ala Ala Cys His Lys Cys Ile Asp
                85                  90                  95

Phe Tyr Ser Arg Ile Arg Glu Leu Arg His Tyr Ile Arg Thr Leu Glu
            100                 105                 110

Asp Leu Leu Met Gly Thr Leu Gly Ile Val Cys Pro Ile Cys Ser Gln
        115                 120                 125

Lys Pro
    130

<210> SEQ ID NO 3
<211> LENGTH: 168
<212> TYPE: PRT
<213> ORGANISM: Artificial sequence
<220> FEATURE:
<223> OTHER INFORMATION: Synthetic polypeptide

<400> SEQUENCE: 3

Met Ser Ala Ala Lys Phe Val Ala Ala Trp Thr Leu Lys Ala Ala Ala

```
                    1               5              10              15
Ser Asp Ser Gly Ile Leu Gly Phe Val Phe Thr Leu Lys Ala Ala Ser
                    20              25              30

Ile Ile Asn Phe Glu Lys Leu Ala Ala Ala Cys Thr Glu Leu Gln Thr
                    35              40              45

Thr Ile His Asp Ile Ile Leu Glu Cys Val Tyr Cys Lys Gln Gln Leu
                    50              55              60

Pro His Ala Ala Cys His Lys Cys Ile Asp Phe Tyr Ser Arg Ile Arg
 65                  70              75                          80

Glu Leu Arg His Tyr Thr Pro Thr Leu His Glu Tyr Met Leu Asp Leu
                    85              90              95

Gln Pro Glu Thr Thr Asp Leu Tyr Cys Tyr Glu Ile Arg Thr Leu Glu
                   100             105             110

Asp Leu Leu Met Gly Thr Leu Gly Ile Val Cys Pro Ile Cys Ser Gln
                   115             120             125

Glu Asp Leu Leu Met Gly Thr Leu Gly Ile Val Cys Pro Ile Cys Ser
                   130             135             140

Gln Lys Pro Ala Asp Asp Leu Arg Ala Phe Gln Gln Leu Phe Leu Asn
145                 150             155                         160

Thr Leu Ser Phe Val Cys Pro Trp
                   165
```

<210> SEQ ID NO 4
<211> LENGTH: 210
<212> TYPE: PRT
<213> ORGANISM: Artificial sequence
<220> FEATURE:
<223> OTHER INFORMATION: Synthetic polypeptide

<400> SEQUENCE: 4

```
Met Lys Lys Leu Leu Ile Ala Ala Met Met Ala Ala Ala Leu Ala Ala
 1               5              10              15

Cys Ser Gln Glu Ala Lys Gln Glu Val Lys Glu Ala Val Gln Ala Val
                    20              25              30

Glu Ser Asp Val Lys Asp Thr Ala Gly Ser Met Ser Ala Ala Lys Phe
                    35              40              45

Val Ala Ala Trp Thr Leu Lys Ala Ala Ala Ser Asp Ser Gly Ile Leu
                    50              55              60

Gly Phe Val Phe Thr Leu Lys Ala Ala Ser Ile Ile Asn Phe Glu Lys
 65                  70              75                          80

Leu Ala Ala Ala Cys Thr Glu Leu Gln Thr Thr Ile His Asp Ile Ile
                    85              90              95

Leu Glu Cys Val Tyr Cys Lys Gln Gln Leu Pro His Ala Ala Cys His
                   100             105             110

Lys Cys Ile Asp Phe Tyr Ser Arg Ile Arg Glu Leu Arg His Tyr Thr
                   115             120             125

Pro Thr Leu His Glu Tyr Met Leu Asp Leu Gln Pro Glu Thr Thr Asp
                   130             135             140

Leu Tyr Cys Tyr Glu Ile Arg Thr Leu Glu Asp Leu Leu Met Gly Thr
145                 150             155                         160

Leu Gly Ile Val Cys Pro Ile Cys Ser Gln Glu Asp Leu Leu Met Gly
                   165             170             175

Thr Leu Gly Ile Val Cys Pro Ile Cys Ser Gln Lys Pro Ala Asp Asp
                   180             185             190

Leu Arg Ala Phe Gln Gln Leu Phe Leu Asn Thr Leu Ser Phe Val Cys
                   195             200             205
```

Pro Trp
    210

<210> SEQ ID NO 5
<211> LENGTH: 8
<212> TYPE: PRT
<213> ORGANISM: Artificial sequence
<220> FEATURE:
<223> OTHER INFORMATION: Synthetic polypeptide

<400> SEQUENCE: 5

Ser Ile Ile Asn Phe Glu Lys Leu
1               5

<210> SEQ ID NO 6
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 6

Gly Ile Leu Gly Phe Val Phe Thr Leu
1               5

<210> SEQ ID NO 7
<211> LENGTH: 10
<212> TYPE: PRT
<213> ORGANISM: Artificial sequence
<220> FEATURE:
<223> OTHER INFORMATION: Synthetic polypeptide

<400> SEQUENCE: 7

Tyr Met Leu Asp Leu Gln Pro Glu Thr Thr
1               5                   10

<210> SEQ ID NO 8
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 8

Leu Leu Met Gly Thr Leu Gly Ile Val
1               5

<210> SEQ ID NO 9
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 9

Phe Gln Gln Leu Phe Leu Asn Thr Leu
1               5

<210> SEQ ID NO 10
<211> LENGTH: 8
<212> TYPE: PRT
<213> ORGANISM: Artificial sequence
<220> FEATURE:
<223> OTHER INFORMATION: Synthetic polypeptide

<400> SEQUENCE: 10

Thr Leu Gly Ile Val Cys Pro Ile

<210> SEQ ID NO 11
<211> LENGTH: 10
<212> TYPE: PRT
<213> ORGANISM: Artificial sequence
<220> FEATURE:
<223> OTHER INFORMATION: Synthetic polypeptide

<400> SEQUENCE: 11

Thr Ile His Asp Ile Ile Leu Glu Cys Val
1               5                   10

<210> SEQ ID NO 12
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 12

Lys Cys Ile Asp Phe Tyr Ser Arg Ile
1               5

<210> SEQ ID NO 13
<211> LENGTH: 27
<212> TYPE: DNA
<213> ORGANISM: Artificial sequence
<220> FEATURE:
<223> OTHER INFORMATION: Synthetic polynucleotide

<400> SEQUENCE: 13
ggaattccat atgaccccga ccctgca                                27

<210> SEQ ID NO 14
<211> LENGTH: 28
<212> TYPE: DNA
<213> ORGANISM: Artificial sequence
<220> FEATURE:
<223> OTHER INFORMATION: Synthetic polynucleotide

<400> SEQUENCE: 14
ccgctcgagc ggtttctggc tgcaaatc                              28

<210> SEQ ID NO 15
<211> LENGTH: 27
<212> TYPE: DNA
<213> ORGANISM: Artificial sequence
<220> FEATURE:
<223> OTHER INFORMATION: Synthetic polynucleotide

<400> SEQUENCE: 15
cgggatccat gagcgcggcg aaatttg                               27

<210> SEQ ID NO 16
<211> LENGTH: 25
<212> TYPE: DNA
<213> ORGANISM: Artificial sequence
<220> FEATURE:
<223> OTHER INFORMATION: Synthetic polynucleotide

<400> SEQUENCE: 16
ccgctcgagc cacggacaca caaag                                 25